United States Patent
Krause

(10) Patent No.: US 10,653,300 B2
(45) Date of Patent: May 19, 2020

(54) METHOD FOR JOINING TWO COMPONENTS OF A MEDICAL INSTRUMENT, USE OF AN IRON-BASED SOLDER, AND MEDICAL INSTRUMENT

(71) Applicant: KARL STORZ GmbH & Co. KG, Tuttlingen (DE)

(72) Inventor: Bernd Krause, Tuttlingen (DE)

(73) Assignee: KARL STORZ SE & Co. KG, Tuttlingen (DE)

(*) Notice: Subject to any disclaimer, the term of this patent is extended or adjusted under 35 U.S.C. 154(b) by 729 days.

(21) Appl. No.: 15/228,330

(22) Filed: Aug. 4, 2016

(65) Prior Publication Data
US 2017/0035269 A1    Feb. 9, 2017

(30) Foreign Application Priority Data
Aug. 4, 2015   (DE) .................. 10 2015 009 858

(51) Int. Cl.
*A61B 1/00*    (2006.01)
*A61B 1/267*   (2006.01)
(Continued)

(52) U.S. Cl.
CPC ............ *A61B 1/0011* (2013.01); *A61B 1/267* (2013.01); *B23K 1/0008* (2013.01); *B23K 1/19* (2013.01);
(Continued)

(58) Field of Classification Search
CPC ...... B23K 1/0008; B23K 1/002; B23K 1/005; B23K 1/16; B23K 1/19
See application file for complete search history.

(56) References Cited

U.S. PATENT DOCUMENTS 4,436,697 A   3/1984   Friedrich et al.
4,460,414 A * 7/1984   Hwang .............. B23K 35/3613
                                               148/23
(Continued)

FOREIGN PATENT DOCUMENTS

DE   31 19 725 C2   2/1983
DE   33 17 831 A1  11/1984
(Continued)

OTHER PUBLICATIONS

Oerlikon, "An Introduction to Brazing: Fundamentals, Materials, Processing," Issue 4, at https://www.oerlinkon.com/ecomaXL/files/oerlikon_Introduction_to_Brazing_EN4.pdf, pp. 1-24 (Sep. 30, 2014).
(Continued)

*Primary Examiner* — Anu Ramana
(74) *Attorney, Agent, or Firm* — Muncy, Geissler, Olds & Lowe, P.C.

(57) ABSTRACT

A method is provided for joining at least two components of a medical instrument, the at least two components are held so as to form at least one soldering gap between mutually assigned joining areas of the components, a solder material is arranged for filling the at least one soldering gap, and the arrangement of the at least two components and of the solder material is heated to a soldering temperature of the solder material, wherein the solder material is an iron-based solder. A use of an iron-based solder and a medical instrument, in particular a laryngoscope spatula, are also provided.

9 Claims, 2 Drawing Sheets

(51) Int. Cl.
   B23K 35/30    (2006.01)
   B23K 1/19     (2006.01)
   B23K 1/00     (2006.01)
   B23K 26/21    (2014.01)
   B23K 1/20     (2006.01)
   B23K 28/02    (2014.01)
   B23K 103/04   (2006.01)

(52) U.S. Cl.
   CPC ............. B23K 1/20 (2013.01); B23K 26/21 (2015.10); B23K 28/02 (2013.01); B23K 35/3053 (2013.01); B23K 2103/05 (2018.08)

(56) References Cited

U.S. PATENT DOCUMENTS

| | | | |
|---|---|---|---|
| 5,409,015 A | | 4/1995 | Palermo |
| 5,833,921 A | * | 11/1998 | Paruchuri ............ B23K 35/264 420/589 |
| 8,267,856 B2 | | 9/2012 | Anders |
| 2011/0020166 A1 | | 1/2011 | Otobe et al. |
| 2013/0084467 A1 | | 4/2013 | Sjödin |

FOREIGN PATENT DOCUMENTS

| | | |
|---|---|---|
| DE | 31 45 944 C2 | 12/1988 |
| DE | 694 27 465 T2 | 6/2002 |
| DE | 101 13 706 A1 | 10/2002 |
| EP | 2 151 185 B1 | 2/2012 |
| GB | 2 102 294 A | 2/1983 |

OTHER PUBLICATIONS

Hoyer, "Paper on the Development of High-Temperature Iron-Based Solders," Dissertation for Dept of Mech. Eng., Chemnitz Univ. of Tech., pp. 1-143 (Aug. 23, 2005) with partial English translation (of relevant pages).

Heintzenberg, "Vergleich der mechanischen Festigkeiten goloeteter and lasergeschweisster Pruekoerper aus einer Palladiumbasis-Legierung nach chemischer Belastung," at http://webdoc.sub.gwdg.de/ebook/diss/2003/fu-berlin/2002/148/03_schrifttum_020808.pdf, pp. 20-23 (Sep. 13, 2002) with partial English translation (of relevant pages).

\* cited by examiner

METHOD FOR JOINING TWO COMPONENTS OF A MEDICAL INSTRUMENT, USE OF AN IRON-BASED SOLDER, AND MEDICAL INSTRUMENT

This nonprovisional application claims priority to German Patent Application No. DE 10 2015 009 858.6, which was filed in Germany on Aug. 4, 2015, and which is herein incorporated by reference.

BACKGROUND OF THE INVENTION

Field of the Invention

The present invention relates to a method for joining two components of a medical instrument, a use of an iron-based solder, and a medical instrument.

Description of the Background Art

Medical instruments, in particular invasive medical instruments, which are intended to be introduced into a human or animal body, are subject to special requirements. For reasons of mechanical and thermal loading, such instruments are often produced using metallic materials. In particular, the materials forming the outer surfaces of the instrument have to be biocompatible. If, for structural reasons, the medical instrument is made up of a plurality of individual components, a permanent connection of the components to one another is necessary. The connection has to meet the required strength and also provide sufficient resistance to chemical and thermal influences and satisfy the demands of biocompatibility. If the components connected to one another result in the formation of a cavity in which sensitive or non-biocompatible parts are accommodated, the connection of the components also has to be fluid-tight, for example in order to avoid entry of bodily fluid or of cleaning liquid into the cavity. These requirements apply even more in the case of reusable medical instruments, which have to be suitable for cleaning and sterilizing, in the process of which they are exposed to chemically aggressive substances and, during autoclaving, to an elevated temperature and elevated pressure.

DE 31 19 725 C2 discloses a laryngoscope spatula, which is constructed from two L-shaped elongate profiled members which are fitted together with a mutual overlap and soldered onto each other. Protruding studs are formed on the contact edges of the L-shaped elongate profiled members and engage in grooves formed in the other elongate profiled member, such that a mutual hold is achieved after the elongate profiled members have been fitted to each other. The profiled members are then fixed to each other by resistance-welding, and the remaining gaps are closed by hard soldering.

According to DE 33 17 831 C2, a laryngoscope spatula has a Z-shaped profile and an L-shaped profile, wherein the connection between a first limb of the Z-shaped profile and a central web wall with a shorter limb of the L-shaped profile is configured as a weld seam, which is then finely ground and finely polished. The connection point of a second limb of the Z-shaped profile to the longer limb of the L-shaped profile is produced in a soldering process using so much solder material that a pronounced radius of rounding and a surface substantially free of gaps are obtained.

EP 2 151 185 B1, which corresponds to U.S. Pat. No. 8,267,856, and which is herein incorporated by reference, discloses a laryngoscope spatula with a spatula blade, wherein the spatula blade is produced by provision of an upper shell and a lower shell which each have, in cross section, a first portion and two mutually oppositely extending second and third portions, the second and the third portions of the upper shell and the lower shell are placed flat on each other, and the upper shell and the lower shell are firmly connected to each other by joining of the second and third portions. The upper shell and the lower shell can be soldered peripherally to each other at contact edges forming mutually adjoining edges of the second and third portions.

To connect the individual parts of a conventional laryngoscope spatula by soldering, a copper-based solder is often used. Since copper is not biocompatible, spatulas produced in this way are usually additionally welded and chromium-plated, which entails additional production costs. Moreover, the use of a nickel-based solder is known. On account of the flow characteristics of the nickel-based solder, and in order to obtain a uniform surface, the soldering process is carried out using anti-flux which, however, can cause damage to a furnace in which the soldering takes place and in which the anti-flux evaporates. In addition, only a small gap can be bridged by a nickel-based solder, a rough and porous surface is often obtained, and, furthermore, it is not easy to weld over a soldering seam that has been produced with a nickel-based solder. Other methods for producing cohesive joins, for example laser welding, on the other hand have the disadvantage that the weld seams thereby produced, in particular quite long weld seams, are often not vapor-tight; a vapor-tight configuration of weld seams is necessary, however, for an autoclavable medical instrument that has a cavity containing sensitive electronic and/or optical parts.

DE 31 45 944 C2, which corresponds to U.S. Pat. No. 4,436,697, discloses a soldering alloy composed of 25 to 35% iron, 15 to 25% chromium, 3 to 6% silicon, 1 to 4% molybdenum, with the remainder cobalt, and used to solder parts of dental prostheses that were made from a cobalt/chromium alloy.

SUMMARY OF THE INVENTION

It is therefore an object of the present invention to provide a method for joining at least two components of a medical instrument, in particular of a laryngoscope spatula, and to provide a medical instrument produced by the corresponding method, wherein the aforementioned disadvantages are avoided as far as possible. It is in particular an object of the invention to provide a method for joining at least two components of a medical instrument by means of hard soldering, wherein the at least two components can be firmly and permanently connected to each other in a simple and inexpensive manner, and wherein the soldering seam produced has a corrosion-resistant surface and is biocompatible.

A method according to an exemplary embodiment of the invention serves to join, i.e. permanently connect, at least two components of a medical instrument, in particular of an invasive medical instrument. The components are, for example, metallic components, such as components made from stainless steel, although the components can also be made, at least partially, of another material, for example, another metallic material suitable for use in a medical instrument and for the soldering method.

Firstly, the at least two components to be connected to each other are made available. These are designed in such a way that they each have at least one joining area, wherein the joining areas of the at least two components to be connected to each other are assigned to each other in such a way that they can cooperate to form a soldering gap. The joining areas thus have such a shape that, when the components are held suitably with respect to each other, a gap is formed between the joining areas that has a gap width and gap surface suitable for soldering. The at least two components to be connected to each other are then arranged and held with respect to each other such that at least one soldering gap is formed between the mutually facing joining areas of the components. Those areas of the surface of the components that form the joining areas are thus at a short distance from each other and thereby form the at least one soldering gap. For this purpose, the components can, for example, be held on each other by form-fit engagement, a friction fit or a cohesive fit, or they can also be held in a corresponding device.

Moreover, according to an embodiment of the invention, the solder material is arranged in a manner suitable for the soldering process, i.e. the solder material is arranged, with respect to the at least two components to be connected to each other, in such a way that it at least partially fills the at least one soldering gap after fusion in the soldering process. For this purpose, the solder material can be arranged on the at least one soldering gap or also, for example, in capillary connection to the at least one soldering gap, in particular on in each case one of the components to be connected to each other and forming the at least one soldering gap, or also on several components between which the at least one soldering gap is formed. The solder material can also already be arranged on at least one of the components at a time before the at least two components to be connected to each other are held so as to form the soldering gap. In particular, the solder material can be made available in a predefined amount and arranged in such a way that the at least one soldering gap is filled completely or at least substantially completely.

The resulting arrangement composed of the at least two components of the medical instrument and the solder material, which arrangement can be referred to hereinbelow as a "solder bond", is then heated to a soldering temperature, i.e. in particular to a temperature that corresponds at least to the melting temperature of the solder material but lies in particular below a melting temperature of the material of the at least two components. For this purpose, the solder bond is in particular introduced into a corresponding furnace, where the solder bond is heated to the soldering temperature, for example under vacuum or a protective gas. The solder material thus liquefies, is drawn by capillary forces into the at least one soldering gap and fills the latter completely or partially. After the solder has filled the at least one soldering gap, the arrangement is allowed to cool until the solder material has hardened and the at least two components are firmly connected to each other by the soldered connection. The at least two components are thus cohesively bonded to each other in particular via a weld seam formed by the iron-based solder.

According to an exemplary embodiment of the invention, the solder material can be an iron-based solder, i.e. a solder material based on iron. An iron-based solder contains, for example, approximately 28 to 35 percent by weight of iron and also further constituents, which are contained in smaller proportions by weight than iron. An iron-based solder of this kind, designated B—FeCrNiSiP-1027/1097 according to EN ISO 3677, is sold, for example, by Innobraze (Esslingen, Germany) under the name ML 7813/S.

According to an embodiment of the invention, a permanent connection between the at least two components can be created in a simple and reliable manner by use of iron-based solder, wherein the requirements that are placed on connections of components of medical instruments can be satisfied. Thus, iron-based solder is biocompatible, non-corroding and has more favorable flow characteristics than nickel-based solder. Further steps such as chromium plating are therefore unnecessary, and it is likewise possible to do without anti-flux. Therefore, fewer working steps are needed to make the medical instrument, such that more rapid and cost-effective production is permitted.

The method according to an embodiment of the invention can comprise further steps, for example a preliminary treatment of the components to be connected to each other or of the joining areas. Before or after the production of the soldered connection according to the invention, further assembly steps can take place which, in particular, concern the production of the components to be connected to each other and the further assembly of the medical instrument after the soldered bond has cooled.

Preferably, more than two components can be connected to each other by the method according to the invention. For example, two components can be held in each case in order to form a soldering gap, and the solder material can be arranged on the soldering gap, wherein these steps are carried out for all components to be connected by soldering with iron-based solder, and the resulting solder bond is then heated to carry out the soldering process. However, it is also possible that all of the components to be connected by soldering with iron-based solder are first of all suitably arranged, after which the solder material is arranged for filling the soldering gaps before the solder bond is heated to soldering temperature. It is also possible here that several soldering connections, in particular all soldering connections, of the medical instrument can be generated substantially simultaneously or in a single heating step. In this way, the medical instrument can be produced with a minimum of manufacturing steps.

According to an exemplary embodiment of the invention, the at least two components to be connected to each other can be connected to each other by means of laser welding before the heating, for example, before the solder material is arranged on at least one of the components, in order to form the soldering gap between the joining areas. The at least two components can be connected to each other at only a few locations by means of laser spot welding. The formation of only a few weld spots is possible with minimal effort and makes it possible to create a solder bond which is sufficiently strong to permit simple handling, and which ensures a predefined gap width of the at least one soldering gap. Moreover, it is in this way possible, for example, to dispense with an auxiliary device for holding the at least two components. The production of the medical instrument can be further simplified in this way.

The at least two components of the medical instrument that are to be connected to each other can be designed in such a way that during arrangement a cavity is formed between them to form the at least one soldering gap. For example, the iron-based solder for filling the soldering gap can be arranged inside the cavity. For this purpose, the at least two components can initially be held to form the cavity and, thereafter, the iron-based solder can be introduced into the cavity and in particular applied to at least one inner wall of the cavity adjoining the soldering gap, preferably to two inner walls adjoining the soldering gap. However, the iron-based solder can also be applied to at least one of the parts to be connected before these form the cavity, and then the at least two parts are arranged so as to form the cavity. On being heated to the soldering temperature, the solder passes from the inside into the soldering gap and fills the latter. By virtue of the fact that the solder material is delivered to the soldering gap from the direction of the inside, it is easily possible to obtain a soldering seam that is clean and smooth at least on the outside, for example without the need to affix boundaries to prevent running of the solder.

The solder material, which is an iron-based solder, can be made available as a solder paste, for example as a metal powder which has a binder added to it and forms a pasty solder material. This is introduced in particular into the cavity formed between the at least two components. For this purpose, it is possible, for example, to use an applicator which comprises a dosing device and a syringe needle, wherein the dosing device allows a predefined amount of the solder material to be dispensed, and the syringe needle is adapted in terms of its length and, if appropriate, curvature to the shape and size of the cavity. By actuation of the dosing device, the pasty solder material can thus be introduced through an opening of the cavity and applied by the syringe of the syringe needle to at least one inner wall of the cavity, in particular to the at least one soldering gap. In this way, it is easily possible to arrange a desired amount of the solder material for filling the soldering gap and for creating a smooth soldering seam.

Advantageously, after the heating, the cavity is closed off by at least one fluid-tight soldering seam. The cavity can be closed off in other partial areas by further methods. Thus, the cavity can be designed in an elongate form, for example, wherein the side walls of the cavity are formed by the at least two components of the medical instrument that are connected to each other by the at least one fluid-tight soldering seam. At the end faces of the elongate cavity, the latter can be closed off, for example, by the components themselves or by an adhesively bonded or soldered-in closure element. To produce a fluid-tight and in particular vapor-tight connection, the solder material can be introduced in such an amount, and in such a distribution along the soldering gap, that the soldering gap is filled continuously. In particular, an amount of the solder material defined on the basis of the volume of the soldering gap to be filled, and optionally on the basis of any resulting concave fillets of the soldering seam, can be applied uniformly along the soldering gap by the applicator. In this way, when carrying out the soldering process by melting of the solder material, it is possible that the soldering gap is filled practically completely with the iron-based solder. Therefore, after the solder has cooled and hardened, a fluid-tight soldering seam is obtained which permits a vapor-tight closure of the cavity. In this way, it is possible, in a simple and reliable manner, to use the cavity also in autoclavable medical instruments to accommodate electronic and/or optical parts that are sensitive to penetration of vapor.

After the soldering process has been carried out, i.e. after the solder material has penetrated the at least one soldering gap and has at least partially filled the latter, and after the iron-based solder has cooled and hardened, the at least one soldering seam formed by the iron-based solder can be overwelded. In this way, the strength of the connection of the at least two components can be further increased. According to this aspect of the invention, it has been found that a soldering seam formed by iron-based solder can be easily overwelded and, for example, does not tend to form cracks.

The overwelded soldering seam can be smoothed, for example by grinding and/or polishing. The surface quality can be improved in this way, such that cleaning of the medical instrument is made easier in particular.

The invention moreover relates to the use of an iron-based solder for joining at least two components of a medical instrument. According to the invention, it has been found that, with cohesive joining by means of hard soldering using an iron-based solder, a permanent connection between the at least two components can be obtained in a particularly simple and reliable manner, wherein the demands placed on medical instruments can be safely met. This permits particularly cost-effective production of a laryngoscope spatula, for example. In particular the above-described method can be applied using iron-based solder for joining at least two components of the medical instrument.

A medical instrument according to the invention comprises at least two components, which have been connected to each other according to the above-described method or by hard soldering using iron-based solder. The at least two components of the medical instrument that are joined to each other are thus connected to each other by at least one soldering seam, which has been produced according to the above-described method or has been created using iron-based solder. Preferably, the at least two components are produced from stainless steel at least in their respective joining area or in their respective joining areas. With the method according to the invention, components of this kind can be connected to each other particularly firmly and reliably and are moreover suitable for medical uses. A medical instrument of this kind, in particular a laryngoscope spatula, can thus be configured in a particularly simple manner to meet the demands placed on medical instruments, in particular on invasive medical instruments.

The medical instrument can be designed, for example, as a laryngoscope spatula having a base blade and a cover blade which are connected to each other by the method according to the invention and thus via at least one soldering seam formed by an iron-based solder. The base blade and the cover blade enclose a cavity which extends in the longitudinal direction of the spatula and which is limited at least at one end in a fluid-tight manner by the at least one soldering seam created by the method according to the invention. For example, the cavity can be closed off laterally by the base blade and the cover blade and by the fluid-tight soldering seams formed therebetween, while ends of the cavity in the longitudinal direction are left with openings which can be closed by closure elements. It is possible, for example, for electronic and/or optical parts to be accommodated in the cavity that has thus been closed off in a vapor-tight manner. By virtue of the fluid-tight closure of the cavity, it is possible for the laryngoscope spatula to be autoclaved.

The medical instrument can have at least one further component, which is connected to one of the at least two interconnected components via at least one further soldering seam that has been produced by the method described above. In a laryngoscope spatula according to the invention, the at least one further component is, for example, an atraumatic bead arranged at a distal end of the laryngoscope spatula and/or a spatula head arranged at a proximal end of the laryngoscope spatula, which head can have a mechanical coupling and, if appropriate, electrical and/or optical couplings for attachment to corresponding elements of a handle of the laryngoscope.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
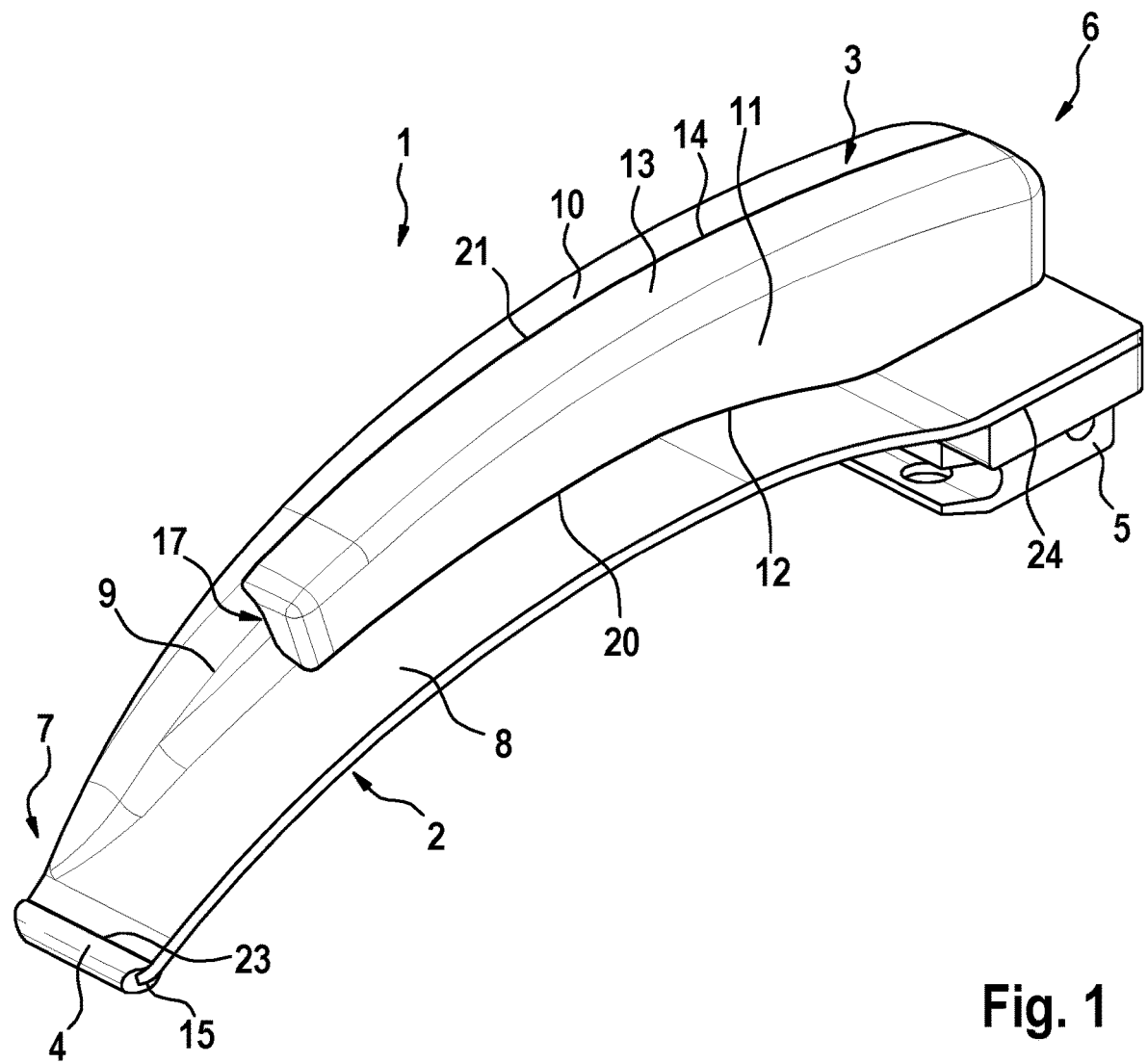
FIG. 1 shows a laryngoscope spatula according to an illustrative embodiment of the invention, in an oblique view.
Figure 2:
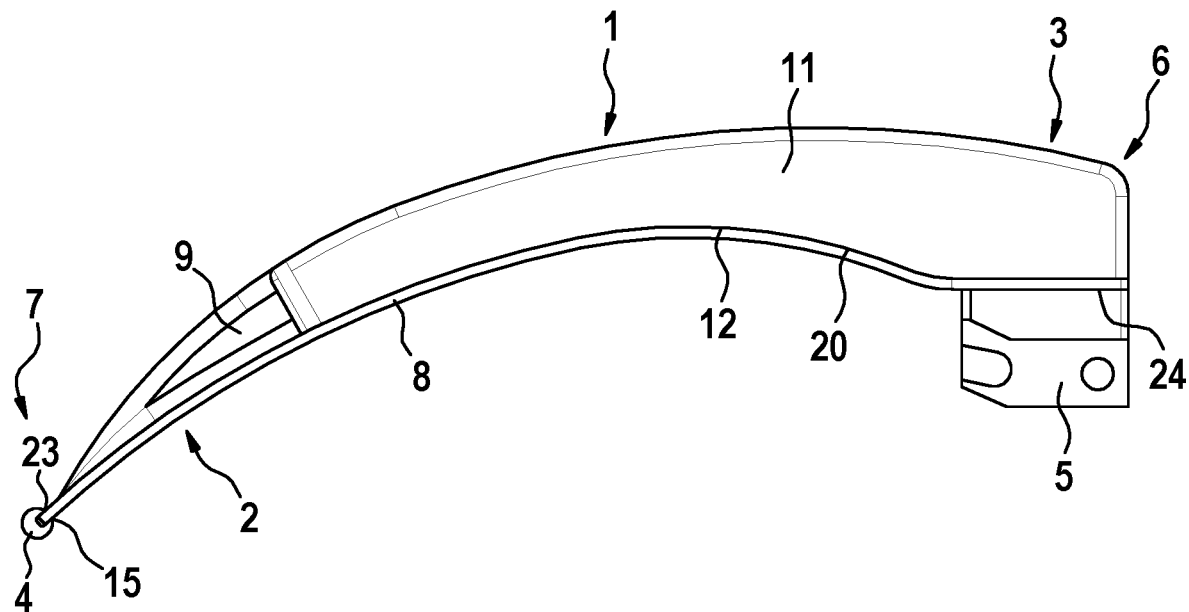
FIG. 2 shows the laryngoscope spatula according to FIG. 1 in a lengthwise view.

In FIGS. 1 and 2, a laryngoscope spatula 1 according to an illustrative embodiment of the invention is shown in an oblique view and a side view, respectively. The laryngoscope spatula 1 comprises four components, which are connected to one another in a method according to the invention, namely a base blade 2, a cover blade 3, a bead 4, and a spatula head 5. A handle (not shown in the figures) can be attached to the spatula head 5 arranged at the user (proximal) end 6 of the laryngoscope spatula 1, with which handle the laryngoscope spatula 1 can be held during an examination. The laryngoscope spatula 1 can be inserted into the oropharyngeal space of a patient and, for this purpose, has a flattened, curved shape adapted to the anatomical circumstances of the oropharyngeal space. The bead 4 arranged at the distal end 7 of the laryngoscope spatula 1, i.e. the end remote from the user, permits easy and atraumatic insertion.

The base blade 2 has a lower limb 8, which extends in the longitudinal direction of the laryngoscope spatula 1 and which has a flat, curved underside and a similar upper face. The lower limb 8 is adjoined in the transverse direction by a middle limb 9, which is at an angle to the lower limb 8 and which is in turn adjoined by an upper limb 10 which, seen in the transverse direction, extends substantially parallel to the lower limb 8. In sections, the middle limb 9 stands approximately perpendicular to the lower limb 8 and the upper limb 10. The height of the middle limb 9 decreases overall from the proximal end 6 to the distal end 7, wherein the height of the middle limb 9 reaches a maximum near the proximal end 6 and returns to zero near the distal end 7. Thus, in the area of the proximal end 6 of the laryngoscope spatula 1 and over the greater part of its longitudinal extent, the base blade has an approximately Z-shaped cross section and, in the area of the distal end 7 of the laryngoscope spatula 1, merges into a flat cross-sectional shape. The base blade 2 is formed in one piece and is made of stainless steel.

The cover blade 3 of the laryngoscope spatula 1 comprises a first limb 11, which extends in the longitudinal direction of the laryngoscope spatula 1 and stands approximately perpendicular to the upper face of the lower limb 8 of the base blade 2. The lower edge 12 of the first limb 11 is adapted to the shape of the upper face of the lower limb 8 of the base blade 2. In its upper area, the first limb 11 is adjoined, approximately perpendicularly thereto, by a second limb 13, of which the upper face merges into the upper face of the upper limb 10 of the base blade 2 and forms therewith a substantially continuous curved surface. The side edge 14 of the second limb 13 is for this purpose adapted to the profile of the transition between the middle limb 9 and the upper limb 10 of the base blade 2. The cover blade 3 has an approximately L-shaped cross section, wherein the height of the first limb 11 reaches a maximum near the distal end 6 of the laryngoscope spatula 1 and decreases in the distal direction.

The atraumatic bead 4 is attached to the distal end of the base blade 2, wherein the lower limb 8 of the base blade 2 protrudes into a groove 15 of the bead 4. The spatula head 5 is hollow and has coupling elements for a releasable mechanical connection to the handle (not shown). The cover blade 3, the bead 4 and the spatula head 5 are also each formed in one piece and produced from stainless steel.

The cover blade 3 encloses, with the base blade 2, an elongate cavity 16 (see FIGS. 3a and 3b) which, at the distal end, terminates in an opening 17. At the proximal end 6, the cavity 16 is closed off in a fluid-tight manner by a transverse wall formed integrally with the cover blade 3, but communicates (not shown in the figures) with the interior of the hollow spatula head 5 via an aperture of the base blade 2.

Figure 3A:
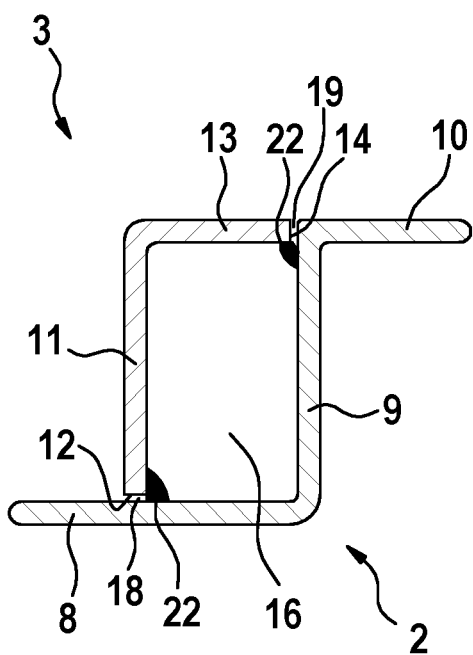
FIGS. 3a and 3b show a cross section through the laryngoscope spatula according to FIGS. 1 and 2 before and after the soldering process is carried out.
Figure 3B:
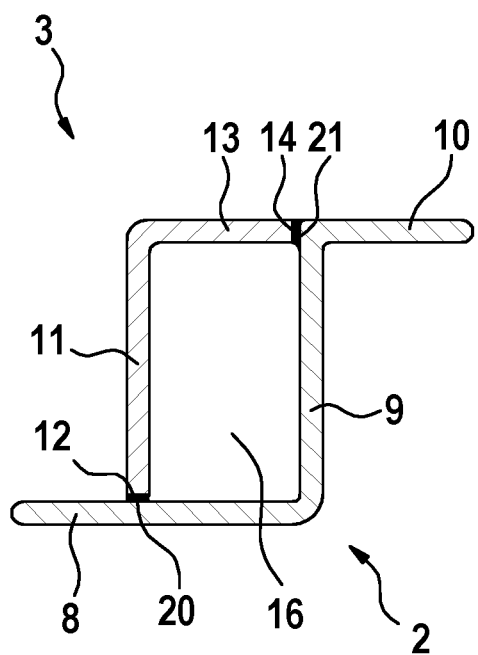

In FIGS. 3a and 3b, the laryngoscope spatula is shown in cross section, the cross-sectional view being approximately at the center of the laryngoscope spatula 1, i.e. the laryngoscope spatula 1 is cross-sectioned approximately half way along its length. FIGS. 3a and 3b show the cavity 16 which is formed between the base blade 2 and the cover blade 3 and which serves to accommodate optical and/or electronic structural elements. The cover blade 3 has joining areas, which are formed by the lower edge 12 and the side edge 14. A partial area of the upper face of the lower limb 8 and the transition from the middle limb 9 into the upper limb 10 constitute the joining areas of the base blade 2, which cooperate with the joining areas of the cover blade 3 in order to form soldering gaps 18, 19 in which soldering seams 20, 21 are generated so as to firmly connect the cover blade 3 to the base blade 2 (see FIG. 3b). This is described in more detail below.

According to an illustrative embodiment of the method according to the invention, the laryngoscope spatula 1 is produced by first of all making available the base blade 2, the cover blade 3, the bead 4 and the spatula head 5. These are then connected to one another by laser spot welding in such a way that they are arranged in the manner shown in the figures, but without yet being connected by soldering seams, and instead each forming a soldering gap 18, 19 between one another. In the next step, a solder material 22, namely iron-based solder in pasty form, is introduced by means of a curved syringe needle through the opening 17 into the cavity 16, in each case using a dosing device to provide an amount necessary to create a soldering seam, and applied to the inner faces of the base blade 2 and of the cover blade 3 adjoining the soldering gaps 18, 19 (see FIG. 3a). For example, the iron-based solder ML 7813/S from Innobraze (Esslingen, Germany) is suitable for this purpose. The solder material 22 in each case forms a bead which adjoins the respective soldering gap 18, 19 from the inside and which bears on the inner walls of both components that between them form the respective soldering gap 18, 19. Likewise, the iron-based solder is introduced into the groove 15 and into the spatula head 5 adjacent to a soldering gap formed between the spatula head 5 and the underside of the base blade 2. For this purpose, for example, a quantity of 0.8 g to 0.9 g is needed for the soldering seams 20, 21 that connect the base blade 2 and the cover blade 3 to each other, and a quantity of 0.5 g to 0.6 g is needed for the soldering seam 24 of the spatula head 5.

This solder bond is then introduced into a furnace and heated to a soldering temperature of approximately 1120° C. The iron-based solider thus liquefies and flows, on account of the capillary action, into the soldering gaps 18, 19 formed between the components to be connected to each other. During the subsequent cooling, which can take place over the course of an hour or a few hours, the iron-based solder hardens in the soldering gaps 18, 19 and forms the soldering seams 20, 21, in order thereby to create a firm, durable and tight connection between the components to be connected to one another. The soldering seams 23, 24 connecting the distal bead 4 and the spatula head 5, respectively, to the base blade 2 are obtained in the same work step. Once cooling is complete, the upper soldering seam 21 between the second limb 13 of the cover blade 3 and the transition from the middle limb 9 to the upper limb 11 of the base blade 2 is overwelded again, in order to increase the strength of the connection, and is then smoothed.

The resulting structure is provided with further components in further steps of the production of the laryngoscope spatula. In particular, optical and electronic structural elements are inserted into the cavity 16. Thus, optical waveguides are inserted into the cavity 16 so that illumination light generated by means of an external light source is conveyed to the distal opening 17 of the cavity 16, or electrical lines are inserted to power a light source arranged in the area of the opening 17. In the area of the opening 17, a viewing lens and an electronic image recorder can be inserted into the cavity 16. Moreover, electrical lines for powering the electronic image recorder and for transmitting signals can be inserted into the cavity 16, likewise an image conductor for forwarding a recorded image. The optical waveguides and/or electrical lines are inserted proximally through an opening (not shown in the figures) of the base blade 2 into the spatula head 5, into which coupling elements are inserted for attachment to corresponding optical waveguides or electrical lines extending inside the handle. By way of these lines, the electronic elements are supplied with electrical energy and the recorded image of the oropharyngeal space of the patient is conveyed to an external display device.

The opening 17 can be closed, for example, by a transparent window or by a video module which contains the viewing lens and the electronic image recorder. The passage between the cavity 16 and the spatula head 5 is likewise closed in a vapor-tight manner at the proximal end. Since the soldering seams are smooth and vapor-tight, the optical and electronic structural elements arranged in the cavity 16 are protected against entry of vapor during autoclaving.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A method for joining at least two components of a medical instrument, the method comprising:
    holding the at least two components so as to form at least one soldering gap between joining areas of the at least two components;
    arranging a solder material for filling the at least one soldering gap, the solder material being an iron-based solder; and
    heating the arrangement of the at least two components and the solder material to a soldering temperature of the solder material,
    wherein the at least two components for forming the at least one soldering gap are connected to each other by laser welding before the heating.

2. The method according to claim 1, wherein a cavity is formed between the at least two components, and wherein the solder material is arranged inside the cavity.

3. The method according to claim 1, wherein the solder material is arranged in a pasty form.

4. The method according to claim 1, wherein at least one soldering seam formed by the solder material and the heating is fluid-tight.

5. The method according to claim 1, wherein at least one soldering seam formed by the solder material and the heating is overwelded.

6. The method according to claim 5, wherein the at least one overwelded soldering seam is smoothed.

7. The method according to claim 1, wherein the medical instrument is a laryngoscope spatula.

8. The method according to claim 1, wherein the at least two components are held so that the joining areas of the at least two components are spaced apart from one another to form the at least one soldering gap.

9. A method for joining at least two components of a medical instrument, the method comprising:
    holding the at least two components so as to form at least one soldering gap between joining areas of the at least two components;
    arranging a solder material for filling the at least one soldering gap, the solder material being an iron-based solder; and
    heating the arrangement of the at least two components and the solder material to a soldering temperature of the solder material,
    wherein a cavity is formed between the at least two components, and wherein the solder material is arranged inside the cavity, and
    wherein the solder material is arranged inside of the cavity prior to the heating of the solder material to the soldering temperature.

* * * * *